United States Patent
Pelerossi et al.

(10) Patent No.: US 7,302,949 B2
(45) Date of Patent: Dec. 4, 2007

(54) HIGH FLOW HUMIDIFIER FOR DELIVERING HEATED AND HUMIDIFIED BREATHING GASES

(75) Inventors: Richard K. Pelerossi, Rome, NY (US); Fredrick M. Richards, Clinton, NY (US); Rex A. Niles, Oneida, NY (US); Gregory S. King, Cazenovia, NY (US)

(73) Assignee: Smiths Medical ASD, Inc., Keene, NH (US)

( * ) Notice: Subject to any disclaimer, the term of this patent is extended or adjusted under 35 U.S.C. 154(b) by 563 days.

(21) Appl. No.: 11/003,527

(22) Filed: Dec. 3, 2004

(65) Prior Publication Data

US 2006/0118111 A1    Jun. 8, 2006

(51) Int. Cl.
A61M 16/16    (2006.01)
A61M 16/10    (2006.01)
H05B 3/78    (2006.01)

(52) U.S. Cl. .......................... 128/200.14; 128/203.17; 128/203.26; 128/203.27; 239/135; 222/56; 261/142

(58) Field of Classification Search ........... 128/200.14, 128/200.16, 203.15, 203.16, 203.17, 204.18, 128/204.21, 204.22, 204.24, 205.12, 205.24, 128/205.27, 206.22, 200.21, 203.26, 203.27, 128/203.25; 239/135, 136, 340, 346, 10, 239/13, 128, 138, 125, 303, 310, 314, 317, 239/378, 548; 261/76, 78.2, 141, 142, DIG. 65; 222/56

See application file for complete search history.

(56) References Cited

U.S. PATENT DOCUMENTS

| | | | | |
|---|---|---|---|---|
| 2,040,630 A | * | 5/1936 | Silten | 128/200.21 |
| 3,667,463 A | * | 6/1972 | Barnes | 128/203.16 |
| 4,101,611 A | * | 7/1978 | Williams | 261/142 |
| 4,178,334 A | * | 12/1979 | Miller | 261/142 |
| 4,190,046 A | | 2/1980 | Virag | |
| 4,195,044 A | * | 3/1980 | Miller | 261/142 |
| 4,243,396 A | * | 1/1981 | Cronenberg | 96/311 |
| 4,391,271 A | | 7/1983 | Blanco | |
| 4,595,002 A | | 6/1986 | Michaels | |
| 4,604,999 A | * | 8/1986 | Maeda | 128/200.21 |
| 4,632,677 A | | 12/1986 | Blackmer | |
| 4,773,410 A | | 9/1988 | Blackmer | |
| 4,805,609 A | * | 2/1989 | Roberts et al. | 128/200.21 |
| 4,877,023 A | | 10/1989 | Zalkin | |
| 4,911,157 A | * | 3/1990 | Miller | 128/200.21 |
| 5,063,921 A | * | 11/1991 | Howe | 128/200.14 |
| 5,195,515 A | * | 3/1993 | Levine | 128/203.26 |
| 5,277,175 A | * | 1/1994 | Riggs et al. | 128/200.21 |
| 5,329,939 A | * | 7/1994 | Howe | 128/203.27 |
| 6,102,037 A | | 8/2000 | Koch | |
| 6,443,154 B1 | | 9/2002 | Jalde | |
| 6,606,994 B1 | | 8/2003 | Clark | |
| 2003/0209246 A1 | | 11/2003 | Schroeder | |
| 2004/0200476 A1 | | 10/2004 | Bamford | |
| 2004/0245658 A1 | | 12/2004 | Niland | |

\* cited by examiner

Primary Examiner—Justine R. Yu
Assistant Examiner—Shumaya B. Ali
(74) Attorney, Agent, or Firm—August E. Roehrig, Jr.; Luedeka, Neely & Graham, P.C.

(57) ABSTRACT

An improved humidifier which may be used with a nasal cannula for high-flow respiratory gas therapy wherein a sterilized liquid is drawn from a sterilized liquid container by a high-flow driving gas passing adjacent to an aspirator tube orifice through which the sterilized liquid is drawn into contact with the driving gas for fracturing the liquid into a mist which is warmed and delivered to the patient or user, and the driving gas is also passed adjacent a condensate return orifice which draws any condensate formed in the humidified respiratory gas delivery system away from the cannula and back into the system for re-use.

15 Claims, 4 Drawing Sheets

HIGH FLOW HUMIDIFIER FOR DELIVERING HEATED AND HUMIDIFIED BREATHING GASES

FIELD OF THE INVENTION

This invention relates in general to an improved humidified respiratory gas delivery system and, in particular, to an improved humidified respiratory gas delivery system wherein breathing gases are warmed and humidified through a heated jet system utilizing a venturi effect. In a preferred closed system embodiment, sterilized water is drawn from a container by a driving respiratory gas which is passed adjacent to a first orifice which draws any condensate formed in the user delivery system back into the system for re-use, and also adjacent a second orifice through which the sterilized liquid is drawn into contact with the driving gas for fracturing the liquid into a mist which is warmed and delivered to the humidifier user.

BACKGROUND OF THE INVENTION

Persons requiring assisted breathing frequently need to have supplemental oxygen delivered to them. Oxygen therapy is widely used in all acute care hospitals and non-acute care settings, being currently prescribed annually to over 70 million patients in acute care hospitals alone. There are few contraindications for oxygen therapy relative to the immediate benefits for many patients in respiratory distress. Current procedure requires a hierarchy of patient interface devices, and the particular device selected depends upon the level of oxygen selected for the treatment. One such interface device considered by many to be the most comfortable is a nasal cannula. The nasal cannula is positioned adjacent to a user's nostrils, and a flow of oxygen, air with supplemental oxygen, heliox or other forms of these or other respiratory gasses, is delivered to the user through the nasal cannula. While nasal cannula are comfortable for users receiving low flow rates of respiratory gases, nasal cannula delivery is too uncomfortable for patients when the flow rate is in excess of 5-6 liters per minute (lpm). When high—or specific—concentrations of oxygen are required, oxygen masks are necessary. Accordingly, a progression of mask systems must be used in response to increased oxygen requirements.

The process of aerosolization of sterile water, and other liquids such as those containing medication, is known to those skilled in the art. A nasal cannula is a preferred mode of delivering such aerosols because it is much more tolerable to a patient, and is less likely to become disengaged. In addition, there are fewer adverse reactions by a patient to the use of a nasal cannula such as facial abrasions caused by the mask, and the patient can eat, speak and drink without removing the cannula through which treatment is being received. It would be very desirable to be able to provide an inexpensive, single-patient-use, high-flow nasal cannula for respiratory care therapy and treatment.

SUMMARY OF THE INVENTION

The present invention is directed to overcoming one or more of the problems or disadvantages associated with the relevant technology. As will be more readily understood and fully appreciated from the following detailed description of a preferred embodiment of the present invention, the invention is embodied in an inexpensive, single-user, disposable respiratory gas delivery system wherein a sterilized liquid is drawn from a container of sterilized liquid by a driving respiratory gas which is passed adjacent to a first orifice which creates a reduced pressure or "vacuum" in a portion of the delivery system to draw any condensate formed in the user delivery system out through the first orifice for re-use in the system. The driving gas is also passed adjacent to a second orifice through which a jet of sterilized liquid is drawn into contact with the driving gas fracturing the liquid into a mist. The particulated mist is then warmed and delivered to the user.

DESCRIPTION OF THE DRAWINGS

Further objectives of the invention, together with additional features contributing thereto and advantages accruing therefrom, will be apparent from the following description of a preferred embodiment of the invention which is shown in the accompanying drawings, wherein.

DETAILED DESCRIPTION OF A PREFERRED EMBODIMENT

Figure 1:
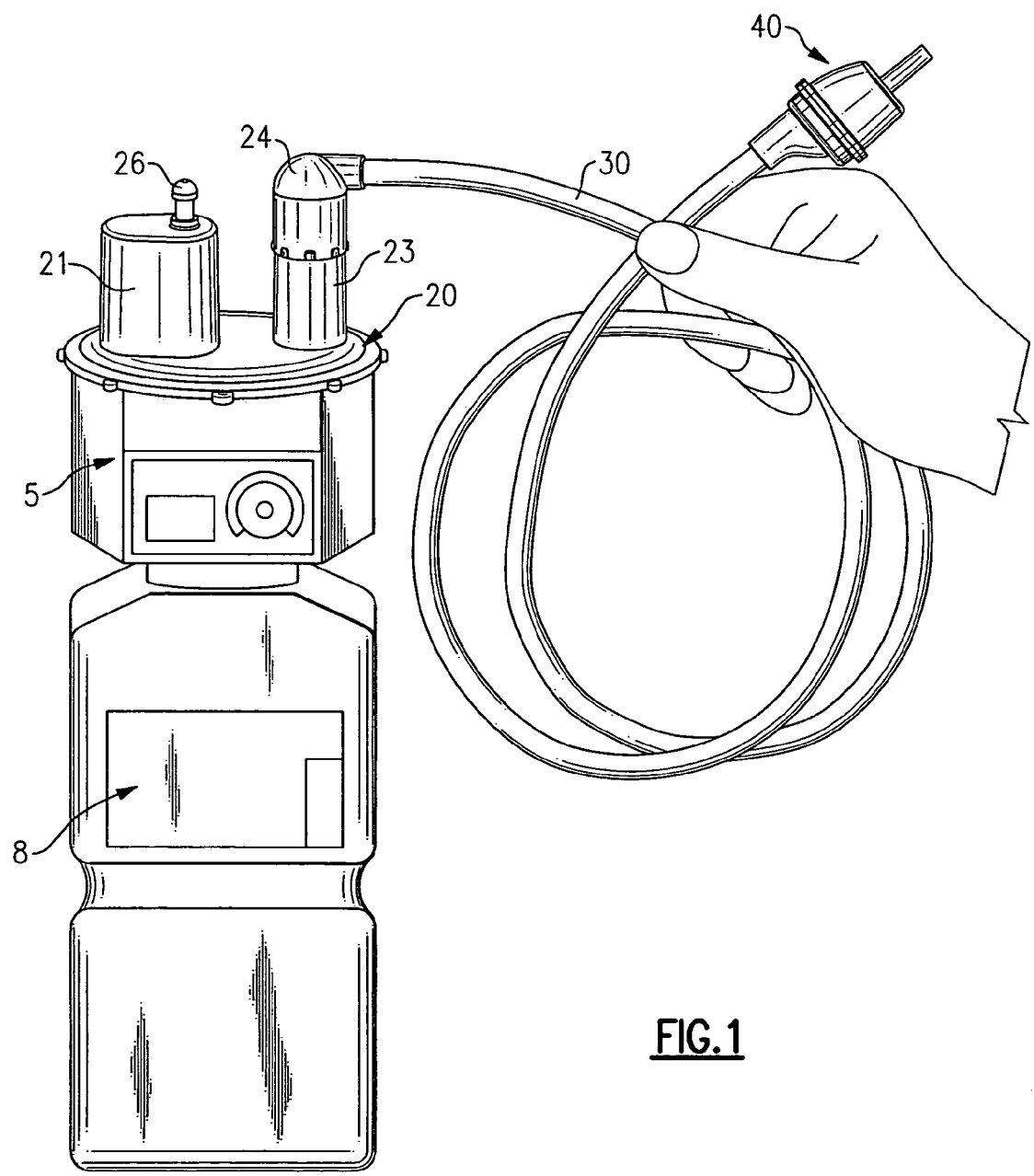
FIG. 1 is a top perspective view of our invention in an application environment.

Referring now to the drawings, there is illustrated a preferred embodiment of an improved humidifier which is preferably primarily molded from plastic and includes a base 10 and a cover 20 which together form a humidity generating chamber 100 in which a liquid, such as sterile water, is vaporized for delivery to a user. The cover 20 includes a mist-generating flow-control chamber 21 in which is carried a liquid-fracturing and suction-force-generating head 22 by which warm moist respiratory gas is produced for delivery to a user, and condensate formed in a delivery conduit 30 is returned to the mist-generating flow-control chamber for re-use.

The base 10 has a bottom heating plate 11 formed from a thermally conductive material for transferring heat energy from a surface contact heater 5, such as a Model No. P20000 heater, available from Smiths Medical ASD, Inc. of Keene, N.H. The lowermost portion of the base 10 has a cylindrical collar 12 extending downwardly therefrom which is internally threaded 13 to receive the external threads of a standard container 8 of sterile water. The upper portion of the collar 12 has a downwardly-sloped or funnel-shaped portion 14 which is positioned to engage the open top of the container 8 when the container is threadingly engaged with the base 10 for forming a liquid-tight seal. The upper portion of the base 10 has an external thread 15 by which the base 10 is engaged with the heater 5 for effective transfer of heat energy from the heater 5 to the heating plate 11.

The cover 20 is sealed to the base 10, and carries the liquid-fracturing and suction-force-generating head 22 and a discharge port 23 through which heated moisture-laden respiratory gas, such as oxygen, heliox, air etc., is discharged to a user or patient. The bottom of the discharge port 23 is open to permit the outward flow of the respiratory gas to the discharge conduit 30 through which the treated gas is transmitted to the user. A distal end of the discharge conduit 30 has coupled thereto a moisture-collecting cannula connector 40 to which is coupled a nasal cannula 9 through which the treated gas is administered to the user.

Figure 2:
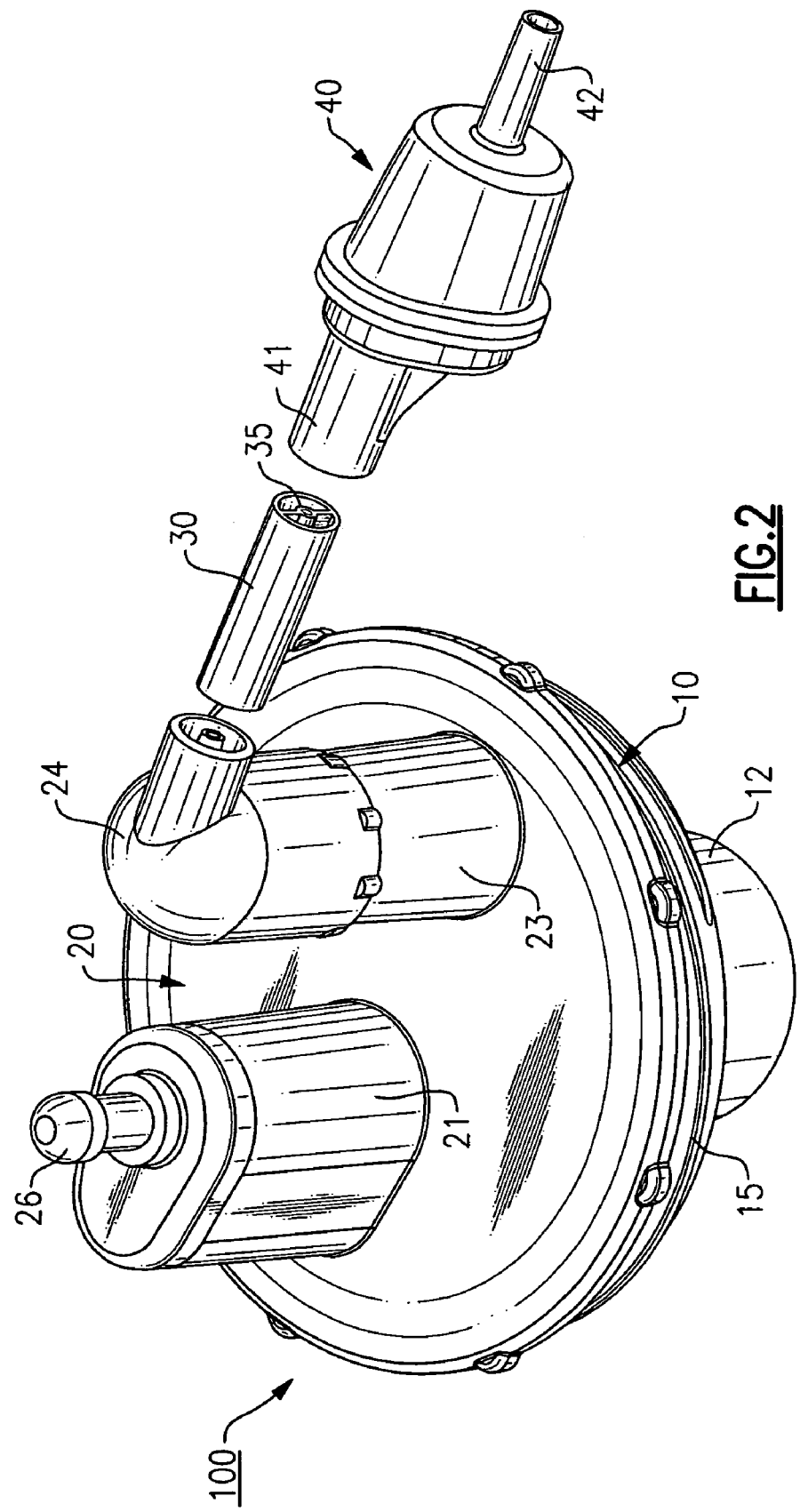
FIG. 2 is a top perspective view of our invention.
Figure 3:
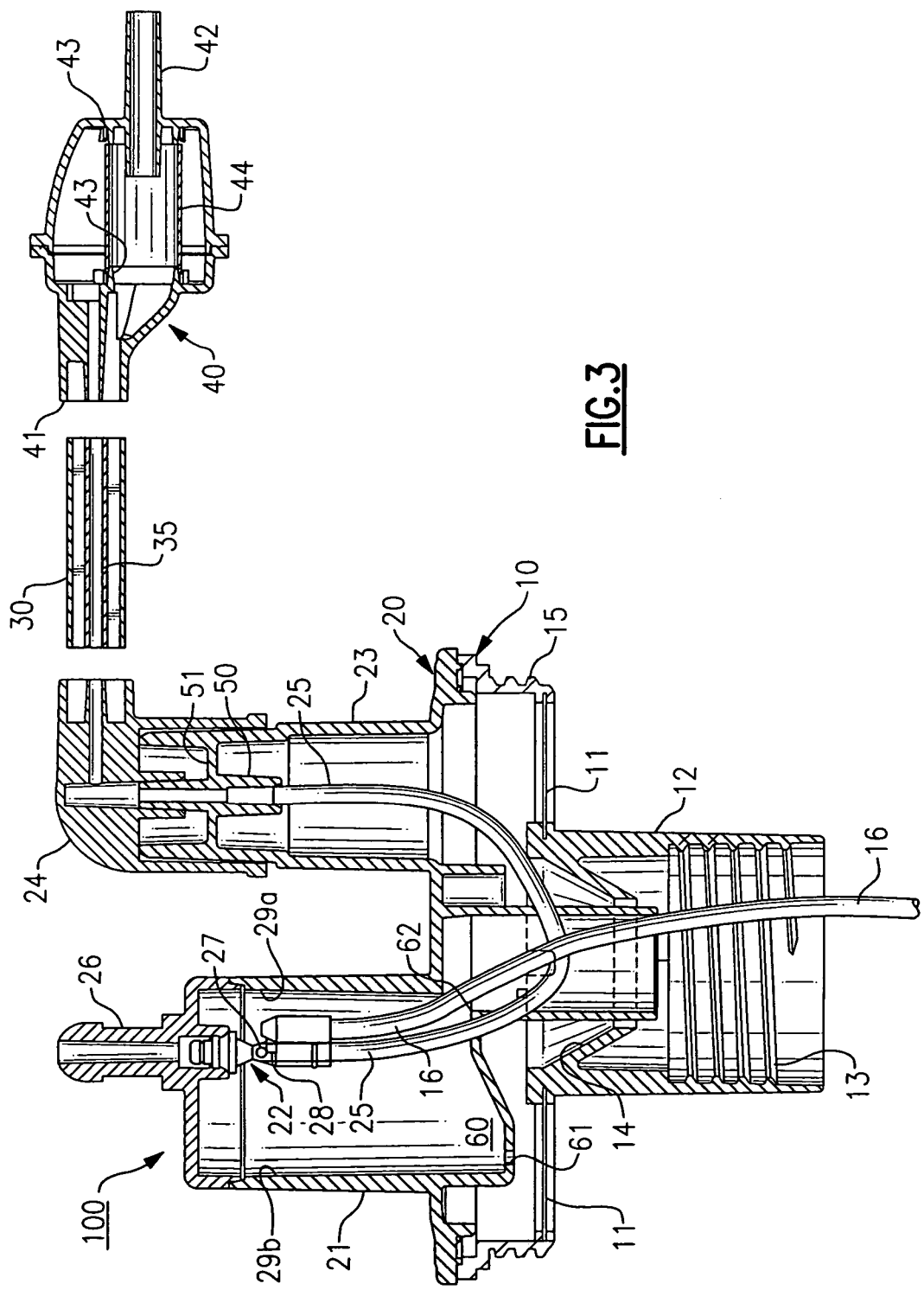
FIG. 3 is a planar cross-sectional view of our invention taken in the general direction of lines 3-3 of FIG. 2.
Figure 4:
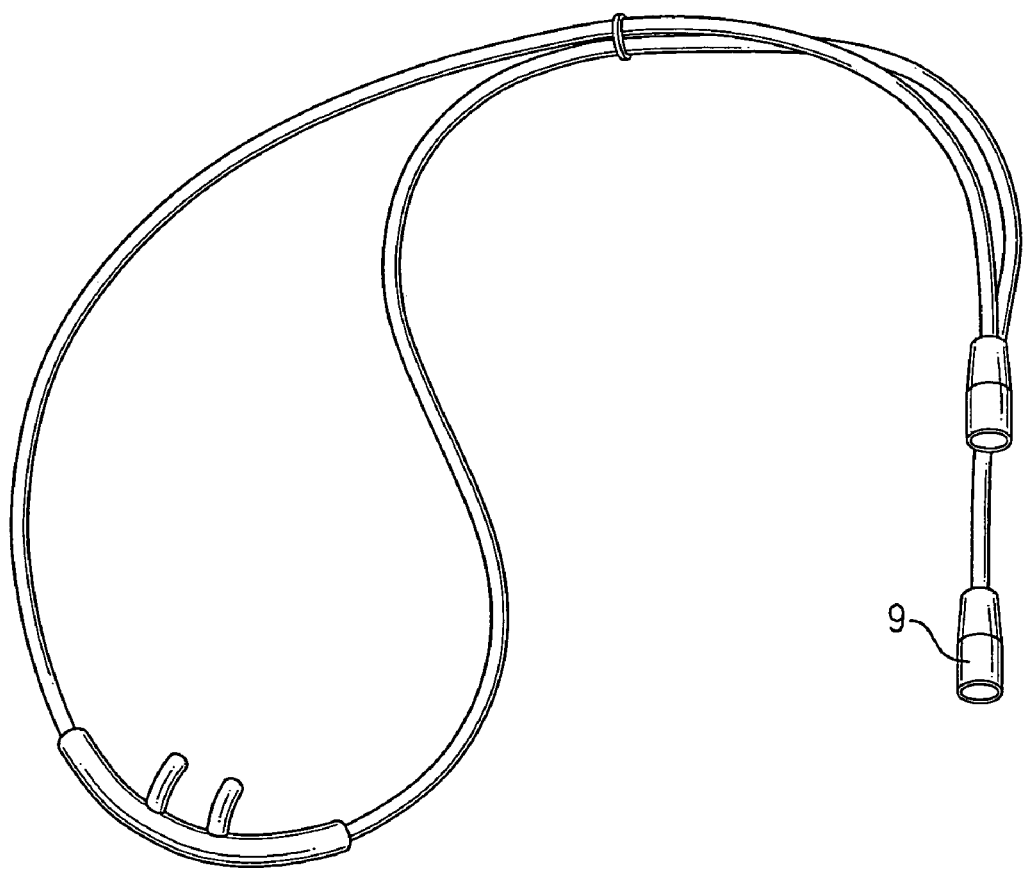
FIG. 4 is a perspective view of a nasal cannula for use with our invention.

The moisture-collecting cannula connector 40 has a proximal end 41 for receiving the distal ends of both the discharge conduit 30 and a condensate conduit 35 to connect these conduits to the moisture collector 40, and a distal end 42 for connection to the nasal cannula 9. As best illustrated in FIG. 2, the moisture collector 40 contains therein a hollow porous polyethylene cylinder 44 which is plasma treated to make the polyethylene more hydrophilic to wick excess moisture from the discharge conduit 30 and the respiratory gas passing therethrough. The polyethylene cylinder 44 is mounted within the moisture collector 40 at each end on an annular rim 43 which suspends the cylinder away from the walls of the moisture collector. In this manner, the cylinder will wick the excess moisture from the discharge conduit 30 and respiratory gasses so that the excess moisture does not pass out through the distal end 42 into the nasal cannula 9. The reduced pressure or vacuum being drawn through the condensate conduit 35 will pull the condensate so removed by the cylinder 44 out from the moisture collector 40 for return to the mist-generating flow-control chamber 21 in a manner to be hereinafter described.

The discharge port 23 also contains a condensate coupler 50, carried on a spider 51, through which the condensate conduit 35 carried within the discharge conduit 30, or formed as a lumen within the discharge conduit 30, is connected. The condensate formed in the discharge conduit 30 as the treated moisture-laden gas is cooled during transmission to the user, is coupled by the condensate conduit 35 through the condensate coupler 50 for return to the system. A discharge tube connector 24 is connected to the proximal end of the discharge conduit 30 and receives the proximal ends of both the discharge conduit 30 and the condensate conduit 35 for connecting these conduits to the discharge port 23 and spider-supported condensate coupler 50, respectively. The moisture laden respiratory gas passes out through the discharge tube connector 24 to be delivered to the patient, and the condensate formed in the discharge conduit 30 is drawn out through the condensate conduit 35, and the condensate coupler 50 carried within the discharge tube connector 24, to a condensate return tube 25 for re-use in the system.

The top of the mist-generating flow-control chamber 21 is formed with an outwardly extending fitting 26 to receive a standard respiratory gas connector on the distal end thereof (not shown) through which is passed a driving respiratory gas for coupling into the humidity generating chamber 100. The proximal end of the fitting 26 extends into the mist-generating flow-control chamber 21, and is connected to the liquid-fracturing and suction-force-generating head 22 through which the driving respiratory gas is introduced to the mist-generating flow-control chamber 21. The respiratory gas passing through the suction-force-generating head 22 causes the condensate formed in the discharge conduit 30 to be drawn out through the condensate conduit 35, and liquid to be drawn out from an aspirator tube 16, extending downwardly into the container 8, for fracturing or particularizing the liquid into a vapor.

To this end, the head 22 is positioned adjacent to and in fluid communication with a venturi-forming condensate return orifice 27 and a venturi-forming aspirator tube orifice 28. The positioning of the head 22 in this manner results in the discharge of the driving respiratory gas across the two orifices 27 and 28, respectively, thereby generating a suction force in the condensate return tube 25, connected at one end to the venturi-forming condensate return orifice 27 and at its other end to the condensate coupler 50 carried by the discharge port 23, and a suction force in the aspirator tube 16, connected at one end to the venturi-forming aspirator tube orifice 28 and extending downwardly into the container 8.

As best illustrated in FIGS. 2 and 3, the outwardly extending fitting 26 is carried adjacent one side of the mist-generating flow-control chamber 21 thereby positioning the liquid-fracturing and suction-force-generating head 22 such that the driving respiratory gas or gasses discharged therethrough are directed across the venturi-forming aspirator tube orifice 28 and the venturi-forming condensate return orifice 27 in a preferred direction and in a preferred sequence. Because it is desired that the clearing of condensate from the discharge conduit 30 be given priority, and the length of the condensate conduit 35 exceeds that of the aspirator tube 16, the discharge of the driving gas is first directed across the venturi-forming condensate return orifice 27, and then across the venturi-forming aspirator tube orifice 28. In this manner, when the flow of driving gas is initiated, the suction for both the condensate return and the withdrawing of liquid from the container 8 will begin. The venturi-forming aspirator tube orifice 28, even though positioned below and to the side of the venturi-forming condensate return orifice 27, will still receive a discharge of driving gas sufficient to withdraw liquid from the container 8, through the aspirator tube 16, into the driving gas to be fractionalized for forming a vapor mist.

To control the heating of the vapor mist discharged through the discharge port 23, the venturi-forming aspirator tube orifice 28 is positioned adjacent one wall 29*a* of the mist-generating flow-control chamber 21 so that the vapor mist so formed is directed against the opposed wall 29*b*. In this manner, the vapor mist created by the driving gas will form droplets on the opposed wall 29*b* which will flow downwardly to a liquid metering chamber 60, formed at the lowermost portion of the mist-generating flow-control chamber 21, and the moisture laden respiratory gas will pass out of the mist-generating flow-control chamber 21 for discharge through the discharge port 23.

The metering chamber 60 has a metering orifice 61 formed in the bottom thereof to meter the flow of liquid droplets onto the heated surface 11 of the base 10. In the event an excess amount of droplets are formed on wall 29*b* and pass into the metering chamber 60, an overflow outlet 62 is formed near the bottom of the metering chamber 60 at a level above the metering orifice 61. This overflow outlet 62 is in fluid communication with the container 8, so that the excess flow to the metering chamber 60 will not affect the metering of the liquid to the heated plate 11, but will be directed into the container 8 for re-use.

While this invention has been described in the specification and illustrated in the drawings with reference to a preferred embodiment, the structure of which has been disclosed herein, it will be understood by those skilled in the art to which this invention pertains that various changes may be made and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims. This application was prepared without reference to any particular dictionary. Accordingly, the definition of the terms used herein conforms to the meaning intended by the inventors acting as their own lexicographer, in accordance with the teaching of the application, rather that any dictionary meaning which is contrary to or different from the inventors' meaning regardless of the authoritativeness of such dictionary.

What is claimed is:

1. A humidifier for providing warm moist respiratory gases, comprising;
   a respiratory gas heating chamber having a closed top, enclosing sides, and an open bottom adapted to receive for coupling thereto a container adapted to contain a liquid to be aerosolized into a vapor;
   a vapor-forming flow-control chamber in fluid communication with said respiratory gas heating chamber for forming an aerosolized vapor from liquid in fluid communication therewith;
   nozzle means in fluid communication with said vapor-forming flow-control chamber for creating an aerosolized vapor from respiratory gas and the liquid in fluid communication with said vapor-forming flow-control chamber;
   a first orifice positioned in fluid communication with said nozzle means such that the flow of respiratory gas from said nozzle means will create a reduced pressure across said first orifice for withdrawing a condensate fluid therethrough;
   a second orifice positioned in fluid communication with said nozzle means and spaced from said first orifice such that the flow of respiratory gas from said nozzle means will create a reduced pressure across said second orifice for withdrawing therethrough liquid contained in a container coupled to said respiratory gas heating chamber;
   heating means for warming the aerosolized vapor created by said nozzle means;
   a discharge port in fluid communication with said vapor-forming fluid-control chamber for delivering the warm aerosolized vapor to a nasal cannula for inhalation by a user; and
   condensate conduit means in fluid communication with said first orifice for withdrawing therethrough condensate formed by the cooling of the warm aerosolized vapor during delivery thereof to the nasal cannula.

2. The apparatus of claim 1 wherein said heating means comprises a surface contact heater.

3. A humidifier for use with a heater for providing warm moist respiratory gases, comprising;
   a respiratory gas heating chamber having a closed top, enclosing sides, and an open bottom adapted to receive for coupling thereto a container adapted to contain a liquid to be aerosolized into a vapor and adapted to receive a heater for warming the aerosolized vapor;
   a vapor-forming flow-control chamber in fluid communication with said respiratory gas heating chamber for forming an aerosolized vapor from liquid in fluid communication therewith;
   nozzle means in fluid communication with said vapor-forming flow-control chamber for creating an aerosolized vapor from respiratory gas and the liquid in fluid communication with said vapor-forming flow-control chamber;
   a first orifice positioned in fluid communication with said nozzle means such that the flow of respiratory gas from said nozzle means will create a reduced pressure across said first orifice for withdrawing a condensate fluid therethrough;
   a second orifice positioned in fluid communication with said nozzle means and spaced from said first orifice such that the flow of respiratory gas from said nozzle means will create a reduced pressure across said second orifice for withdrawing therethrough liquid contained in a container coupled to said respiratory gas heating chamber;
   a discharge port in fluid communication with said vapor-forming fluid-control chamber for delivering the warm aerosolized vapor to a nasal cannula for inhalation by a user; and
   condensate conduit means in fluid communication with said first orifice for withdrawing therethrough condensate formed by the cooling of the warm aerosolized vapor during delivery thereof to the nasal cannula.

4. The apparatus of claim 3 wherein said respiratory gas heating chamber includes a heating plate of thermally conductive material for transferring heat energy to the aerosolized vapor.

5. The apparatus of claim 3 further including a container for containing sterile water, said container adapted to be threadingly engaged with said respiratory gas heating chamber.

6. The apparatus of claim 3 wherein said respiratory gas heating chamber bottom adapted to receive a container for containing a liquid to be aerosolized into a vapor, has a downwardly-shaped portion for engaging the open top of a container when the container is threadingly engaged with said respiratory gas heating chamber.

7. The apparatus of claim 3 wherein said first orifice for withdrawing a condensate fluid therethrough is positioned in closer proximity to said nozzle means than is said second orifice for withdrawing liquid contained in a container coupled to said respiratory gas heating chamber.

8. The apparatus of claim 7 wherein said first orifice and said second orifice are spaced seriatim in fluid communication with said nozzle means.

9. The apparatus of claim 3 wherein said vapor-forming flow-control chamber includes a metering orifice means for metering the flow of condensate formed therein onto said heating plate.

10. The apparatus of claim 3 further including a nose cannula in fluid communication with said discharge port and said condensate communication means.

11. The apparatus of claim 3 wherein said discharge port is coupled to a discharge conduit for deliver of warm aerosolized vapor to the nose cannula.

12. The apparatus of claim 11 wherein said condensate conduit means is carried within said discharge conduit.

13. The apparatus of claim 11 further including a moisture-collection cannula connector in fluid communication with said discharge conduit and said condensate conduit means.

14. The apparatus of claim 13 further including a moisture collecting means carried within said moisture-collecting cannula connector for removing excess moisture from the warm aerosolized vapor and returning such excess moisture to said flow-control chamber.

15. The apparatus of claim 3 wherein said flow-control chamber includes an overflow outlet means in fluid communication with the container for directing excess condensate to the container.

* * * * *